(12) United States Patent
Deng et al.

(10) Patent No.: US 8,115,126 B2
(45) Date of Patent: Feb. 14, 2012

(54) SELF-SEALING CONTROL ARRANGEMENT FOR A MEDICAL INSTRUMENT

(75) Inventors: Wenjie Deng, San Jose, CA (US); William H. L. Chang, Milpitas, CA (US)

(73) Assignee: Stryker Corporation, Kalamazoo, MI (US)

( * ) Notice: Subject to any disclaimer, the term of this patent is extended or adjusted under 35 U.S.C. 154(b) by 367 days.

(21) Appl. No.: 12/462,874

(22) Filed: Aug. 11, 2009

(65) Prior Publication Data

US 2010/0069711 A1 Mar. 18, 2010

Related U.S. Application Data

(60) Provisional application No. 61/192,413, filed on Sep. 18, 2008.

(51) Int. Cl.
*H01H 13/06* (2006.01)
(52) U.S. Cl. .................................................. 200/302.2
(58) Field of Classification Search .... 200/302.1–302.3, 200/293–296, 341
See application file for complete search history.

(56) References Cited

U.S. PATENT DOCUMENTS

| | | | |
|---|---|---|---|
| 4,877,930 A | 10/1989 | Fukuma | |
| 5,004,879 A | 4/1991 | Bernhardt et al. | |
| 5,430,266 A | 7/1995 | Austin, Jr. et al. | |
| 5,728,986 A * | 3/1998 | Bennett et al. | 200/302.1 |
| 5,777,281 A * | 7/1998 | Riddiford | 200/5 A |
| 6,204,463 B1 | 3/2001 | Stringos | |
| 6,459,057 B1 | 10/2002 | Domzalski | |
| 6,461,352 B2 * | 10/2002 | Morgan et al. | 606/34 |
| 6,500,169 B1 * | 12/2002 | Deng | 200/302.2 |
| 6,573,466 B1 * | 6/2003 | Rapp et al. | 200/302.3 |
| 6,608,270 B2 * | 8/2003 | Donofrio et al. | 200/302.1 |
| 6,635,838 B1 * | 10/2003 | Kornelson | 200/302.2 |
| 6,752,816 B2 | 6/2004 | Culp et al. | |
| 7,282,657 B2 * | 10/2007 | Wimmer et al. | 200/302.2 |
| 7,306,592 B2 | 12/2007 | Morgan et al. | |
| 7,608,039 B1 * | 10/2009 | Todd | 200/314 |
| 7,705,258 B2 * | 4/2010 | Geldmacher | 200/341 |
| 2006/0235377 A1 * | 10/2006 | Earley et al. | 606/41 |

FOREIGN PATENT DOCUMENTS

| | | |
|---|---|---|
| CA | 2 605 485 | 10/2006 |
| ES | 2 013 370 | 5/1990 |
| FR | 2800195 A1 | 4/2001 |
| WO | WO 94/18686 | 8/1994 |
| WO | WO 2006/111021 A1 | 10/2006 |

* cited by examiner

*Primary Examiner* — Briggitte R Hammond
(74) *Attorney, Agent, or Firm* — Flynn, Thiel, Boutell & Tanis, P.C.

(57) ABSTRACT

A control arrangement for use in a medical or surgical instrument, which arrangement includes a keypad for providing manual control functions to a user of the instrument, a retainer clip and a sealing member. The keypad and retainer clip are located within an opening formed in the instrument housing, whereby when the retainer clip is assembled to the housing, the retainer clip automatically causes the sealing member to sealingly engage with a corresponding sealing surface defined adjacent the housing opening, without the need for the use of additional sealing agents.

20 Claims, 6 Drawing Sheets

SELF-SEALING CONTROL ARRANGEMENT FOR A MEDICAL INSTRUMENT

CROSS-REFERENCE TO RELATED APPLICATION

This application claims the benefit of U.S. Provisional Application No. 61/192,413, filed Sep. 18, 2008, the disclosure of which is incorporated herein by reference in its entirety.

FIELD OF THE INVENTION

This invention generally relates to a control or switch arrangement for a medical instrument or tool, and specifically to an arrangement which automatically seals itself upon assembly and without the need for a sealing agent.

BACKGROUND OF THE INVENTION

Medical instruments or tools are utilized during surgery for various purposes. In this regard, cutting instruments, such as surgical saws, are utilized to shape and remove bone, for example, for the purpose of preparing a joint for receiving an implant, such as a hip implant. Other types of surgical tools may be used in what are generally termed endoscopic procedures. Endoscopy in the medical field allows internal features of the body of a patient to be viewed without the use of traditional, fully-invasive surgery. Endoscopic imaging systems incorporate an endoscope so as to enable a user to view a surgical site, and endoscopic tools enable non-invasive surgery at the site. Such tools may be shaver-type devices which mechanically cut bone and hard tissue, or radio-frequency (RF) probes which are used to remove tissue via ablation or coagulate tissue to minimize bleeding at the surgical site, to name a few.

In endoscopic surgery, the endoscope is placed in the body at the location at which it is necessary to perform a surgical procedure. Other surgical instruments, such the endoscopic tools mentioned above, are also placed in the body at the surgical site. The surgeon views the surgical site through the endoscope in order to manipulate the tool to perform the desired surgical procedure. Some endoscopes are usable along with a camera head, for the purpose of processing the image data received by the endoscope. The eyepiece of such an endoscope is typically coupled to the camera head, which camera head is connected to a camera control unit.

The development of endoscopes and their companion surgical tools has made it possible to perform minimally invasive surgery that eliminates the need to make a large incision in the patient to gain access to the surgical site. Instead, during endoscopic surgery, small openings, called portals, are formed. One advantage of performing endoscopic surgery is that since the portions of the body that are cut are reduced, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

Surgical instruments, such as surgical saws, shavers, RF devices, camera heads for use in conjunction with endoscopes and other surgical tools, typically incorporate some type of control arrangement located on the instrument which facilitates manual control of the instrument or tool by the surgeon. For example, a conventional RF probe typically includes a control or button arrangement to allow the user to select "CUT" to ablate tissue or "COAG" to coagulate tissue. Similarly, a shaver arrangement typically incorporates a handpiece to which a shaver probe is attached, wherein the handpiece includes a control arrangement with various buttons to control the direction, speed, etc. of the rotating shaver blade. Camera heads usable with endoscopes likewise incorporate control arrangements to allow the user to control various functions of the camera head, such as zoom, pan, white balance, picture, etc.

Due to the type of environment in which the above surgical instruments are utilized, it is necessary to seal internal electrical and mechanical components of the instruments from the external environment, which can have varying humidity levels, or fluids and/or other contaminants present which could harm the instruments and disrupt the functioning thereof. Control arrangements, such as switches, may be mounted in openings formed in the housings of the instruments, and such openings and control arrangements must be adequately sealed from the environment. One known method of sealing control arrangements of this type is to utilize a sealing agent, such as silicone, around the control or switch arrangement at the junction between the arrangement and the instrument housing. Such an arrangement is utilized on the commercially available FORMULA® shaver handpiece used in arthroscopy procedures, as sold by the Assignee hereof. Specifically, the control arrangement includes a keypad including one or more control buttons thereon, which keypad is then held in the housing opening by a cover plate. The cover plate is held in place by screws, and a sealing agent is applied to the juncture between the housing and the cover plate. While this method is effective for its intended purpose, same nonetheless requires additional components and assembly steps during assembly, which can be time-consuming and costly from a manufacturing perspective.

Other known methods include the use of switch components which are permanently press-fit or adhered to the instrument housing. This method, however, accordingly does not allow disassembly of the arrangement, which is sometimes desirable or necessary for maintenance or repair purposes.

In order to obviate or at least minimize the disadvantages of known sealing arrangements, the instant invention includes a control arrangement which cooperates with a housing of the instrument or tool to provide a seal therebetween upon assembly of the control arrangement to the tool housing. The control arrangement includes an actuator member or keypad having a button or buttons thereon associated with a control function of the instrument, a retaining clip configured for securing the control arrangement to the tool housing and a sealing member. The tool housing has a housing wall which defines an opening therein for receiving the control arrangement, and the housing wall includes a sealing surface adjacent the opening. The retaining clip is disposed within a portion of the housing opening defined outwardly of the actuating member, and is resiliently disposed in such opening portion to prevent dislodgement of the control arrangement from the tool housing. Further, the retaining clip, when engaged within the housing opening, causes sealing engagement of the sealing member with the sealing surface of the housing wall automatically upon assembly of the retaining clip to the housing.

This automatic sealing function of the control arrangement when assembled to the tool housing serves to fully seal the arrangement from the exterior environment of the housing, without the need for the application of a sealing agent, such as silicone or the like, to the junction between the control arrangement and the housing.

Figure 1:
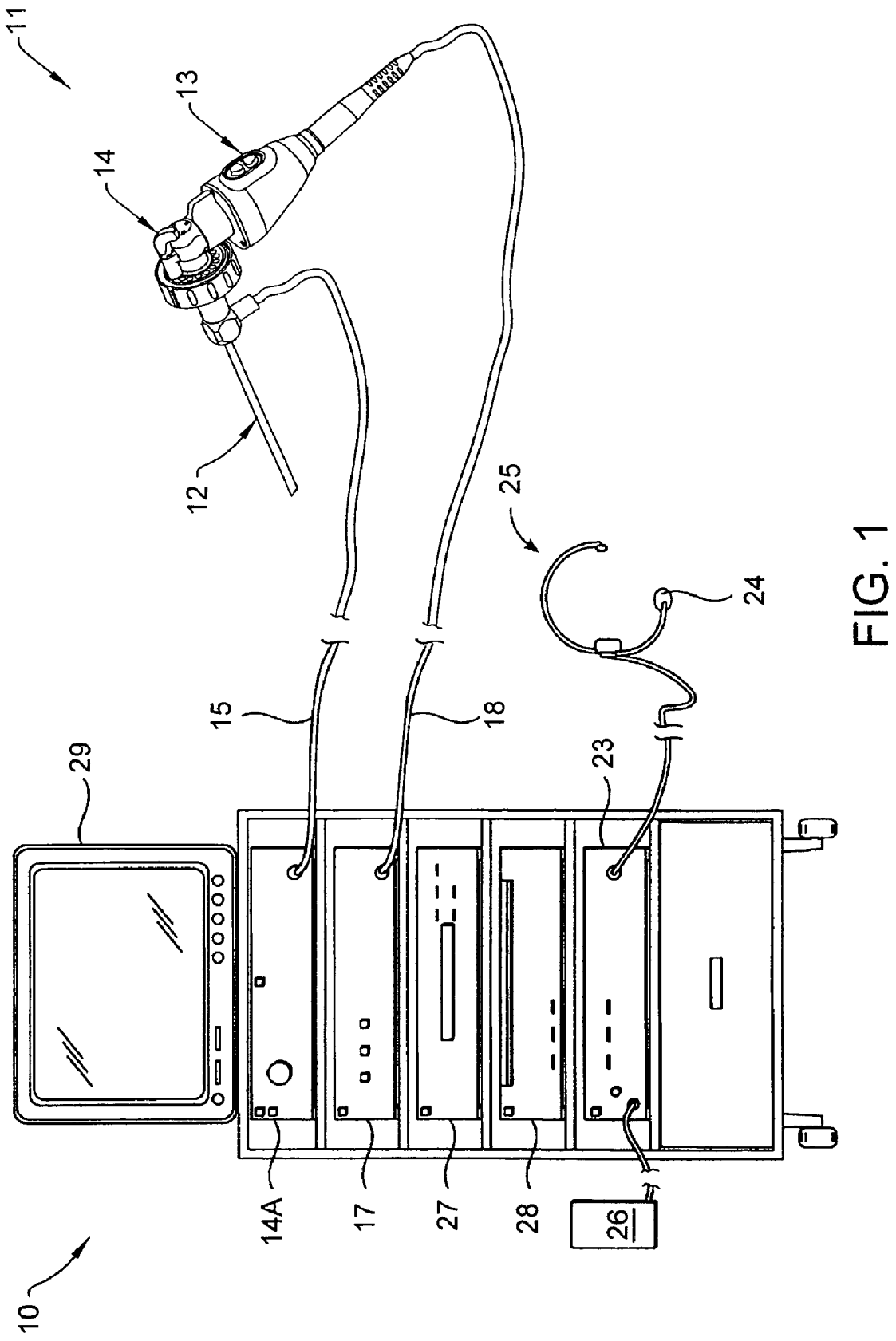
FIG. 1 is an illustration of an endoscopic camera arrangement including an example of one type of scope assembly incorporating a sealed control arrangement pursuant to the invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designed parts thereof. The words "forwardly" and "distally" will refer to the direction toward the end of the arrangement which is closest to the patient, and the words "rearwardly" and "proximally" will refer to the direction away from the end of the arrangement which is furthest from the patient. Said terminology will include the words specifically mentioned, derivatives thereof, and words of similar import.

DETAILED DESCRIPTION

For purposes of illustration, FIG. 1 shows an endoscopic camera arrangement 10, including a scope assembly 11 which may be utilized in endoscopic procedures, for example. The scope assembly 11 incorporates an endoscope or scope 12 which is coupled to a camera head 13 by a coupler 14 located at the distal end of camera head 13. Camera head 13 incorporates well-known circuitry, such as a charge-coupled device (CCD) or a complementary metal oxide semi-conductor (CMOS), for acquiring color video image data of internal features of the body through one or more lenses within the scope 12. Light is provided to the scope 12 by a light source 14A via a light conduit 15, such as a fiber-optic cable. The camera head 13 is coupled to a camera control unit (CCU) 17 by a transmission cable 18. Operation of the camera arrangement 10 is controlled, in part, by CCU 17. Cable 18 conveys video image data from the camera head 13 to the CCU 17 and conveys various control signals bi-directionally between the camera head 13 and the CCU 17. In one embodiment, the image data output by the camera head 13 is digital, in which case cable 18 may be Firewire, a Universal Serial Bus (USB) or another type of high-speed digital interface.

Figure 2:
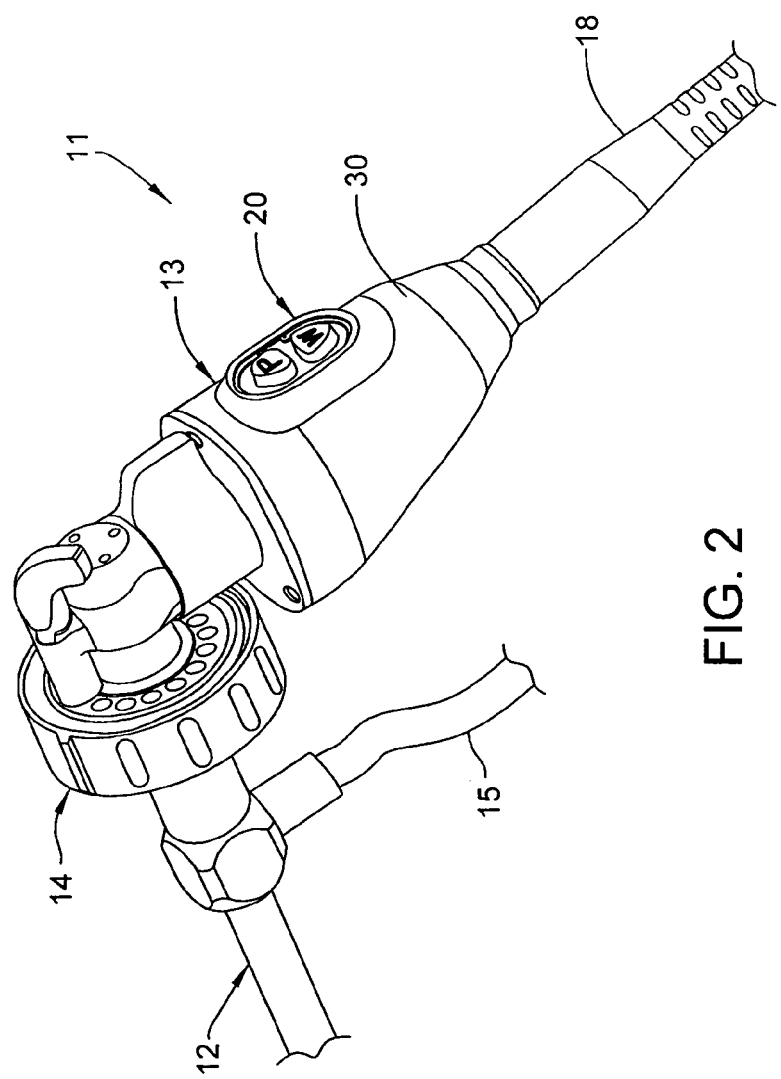
FIG. 2 is an enlarged and fragmentary perspective view of the scope assembly of FIG. 1.

A control or switch arrangement 20 (FIG. 2) is provided on the camera head 13 and allows the user to manually control various functions of the camera arrangement 10. These camera functions may also be controlled by voice commands using a voice control unit 23, which control unit 23 is coupled to CCU 17. Voice commands are input into a microphone 24 mounted on a headset 25 worn by the surgeon and coupled to the voice control unit 23. A hand-held control device 26, such as a tablet with a touch-screen user interface or a pendant, may be coupled to the voice control unit 23 as a further control interface. In the illustrated embodiment, a DVD recorder 27 and a printer 28 are also coupled to the CCU 17. Additional devices, such as an image capture and archiving device, may be included in arrangement 10 and coupled to CCU 17. Video image data acquired by camera head 13 and processed by CCU 17 is converted to images, which can be displayed on a monitor 29, recorded by recorder 27, and/or used to generate static images, hard copies of which images can be produced by printer 28.

With reference to FIGS. 3-6, camera head 13 includes a housing 30 defined by a generally tubular housing wall 31 defining a hollow interior 32. Interior 32 opens distally through an opening 33 which cooperates with coupler 14, and sidewardly through a bore or opening 34 which extends completely through housing wall 31 and mounts therein control or switch arrangement 20. Bore 34 is defined by an annular terminal edge portion of housing wall 31 having multiple stepped sections or portions as described below.

Housing wall 31 includes an annular flange 35 having an inner surface 36 oriented generally transverse to a longitudinal axis A of scope 11 (which axis A is generally parallel to a horizontal plane of bore 34), and generally parallel to a central axis B of bore 34 (which axis B is oriented transversely to axis A). Surface 36 defines a radially innermost portion 38 of bore 34 with respect to scope axis A, and in the illustrated embodiment portion 38 has the smallest diameter of all of the sections of bore 34. Surface 36 is joined to a flat annular surface 39 which is generally parallel to scope axis A and generally perpendicular to bore axis B, which surface 39, in turn, is joined to a further surface 40 of housing wall 31. Surface 40 is essentially perpendicular to axis A and essentially parallel to axis B. Surfaces 39 and 40 are oriented transversely to one another, and in the illustrated embodiment together form a right angle. Further, surface 40 is located axially outwardly from surface 36 with respect to scope axis A, and is generally parallel to surface 36, so as to define an intermediate portion 42 of bore 34 having a larger diameter than adjacent bore portion 38.

An upper extent of surface 40 is joined to an annular sealing surface 44 which protrudes radially relative to scope axis A and is joined to a flat annular surface 45. With respect to axis A, surface 45 is located radially inwardly from surface 44 and axially outwardly therefrom. Surface 45 is joined to a wall surface 48 which is generally parallel to surface 40 and is located axially outwardly (axis A) therefrom so as to define a further bore portion 50 of a larger diameter than adjacent bore portion 42. Surface 48, surface 45 and an outer surface of sealing surface or projection 44 together define an annular recess or notch 49 located immediately adjacent sealing projection 44, and projecting radially inwardly relative thereto with respect to axis A. Surface 48 is joined to a flat annular surface 52 which adjoins an annular housing wall surface 53 located axially outwardly from wall surface 49 (axis A) and generally parallel thereto so as to define a further bore portion 60 of a greater diameter than adjacent bore portion 50, but of a lesser radial dimension than bore portion 50 (axis A).

Bore portion 60 joins to an outermost bore portion 61 defined by an annular housing surface 63 located axially inwardly (axis A) from adjacent housing surface 53 such that housing wall 31 defines an outer flange 65 which overhangs bore portion 60 so as to form a retaining lip therearound. Outermost bore portion 61 is the radially outermost part of bore 34 (axis A). In the illustrated embodiment, flange 65 is annular. However, it will be appreciated that flange 65 may be embodied by a plurality of flanges or projections located about the periphery of bore 34, or only a single flange of an adequate circumferential dimension may be provided along a portion of the outer periphery bore.

Figure 5:
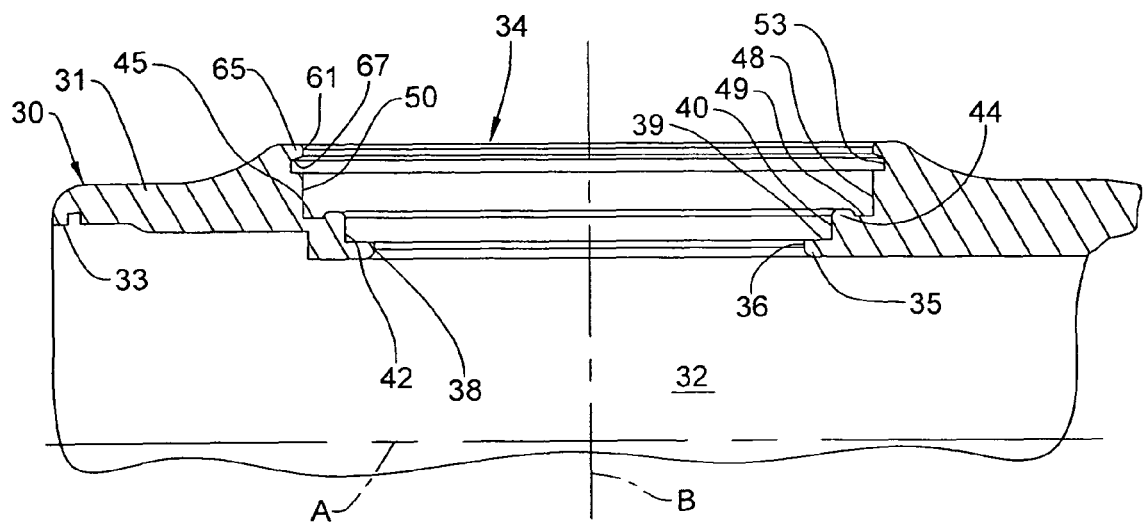
FIG. 5 is an enlarged, fragmentary cross-sectional view of the housing of the camera head as seen generally along line 5-5 in FIG. 3.
Figure 6:
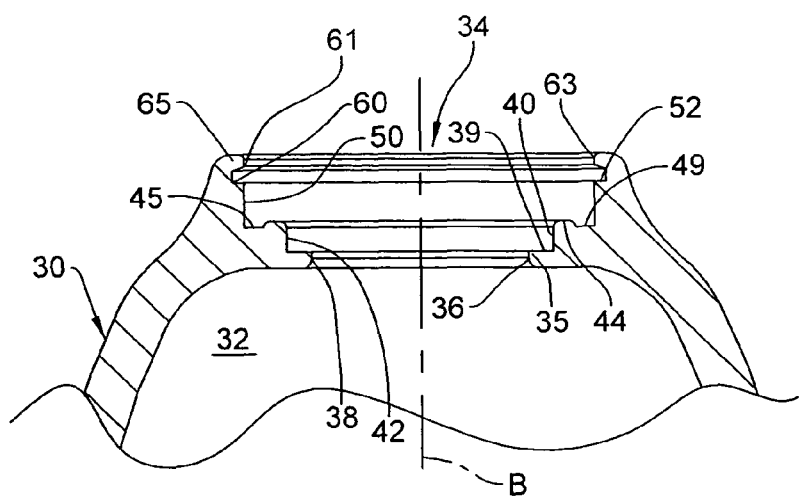
FIG. 6 is an enlarged, fragmentary cross-sectional view of the housing of the camera head as seen generally along line 6-6 in FIG. 3 and rotated clockwise by about 90 degrees.

With reference to FIGS. 5 and 6, in the illustrated embodiment, flange 65 angles upwardly as same projects radially inwardly with respect to and towards axis B, and thus defines a slightly upwardly inclined inner surface 67 which is oriented at an angle in the range of about 15-20 degrees relative to axis A.

Figure 3:
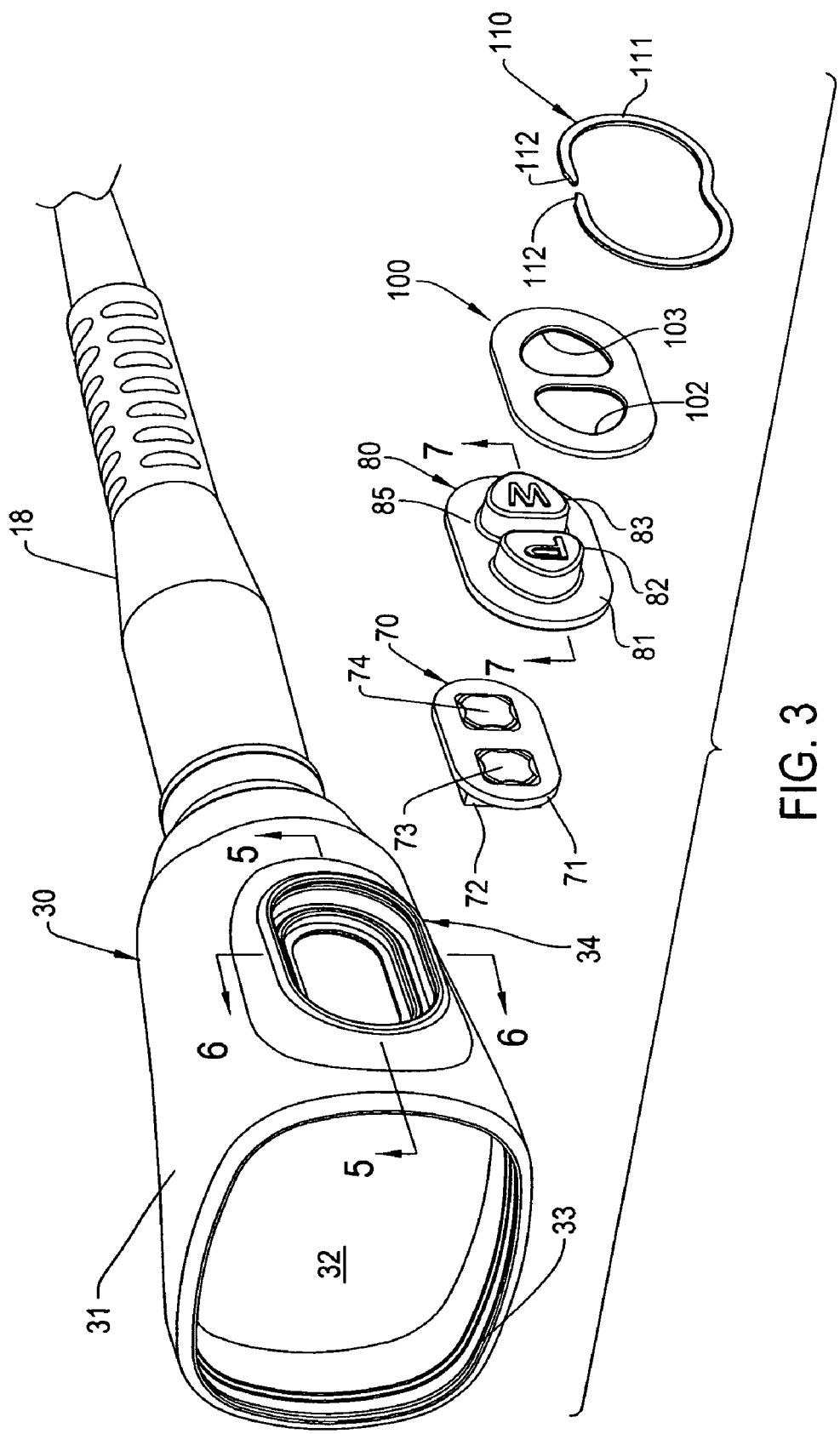
FIG. 3 is an enlarged and fragmentary exploded perspective view of portions of the scope assembly of FIG. 1, illustrating the various components of the control or switch arrangement.
Figure 11:
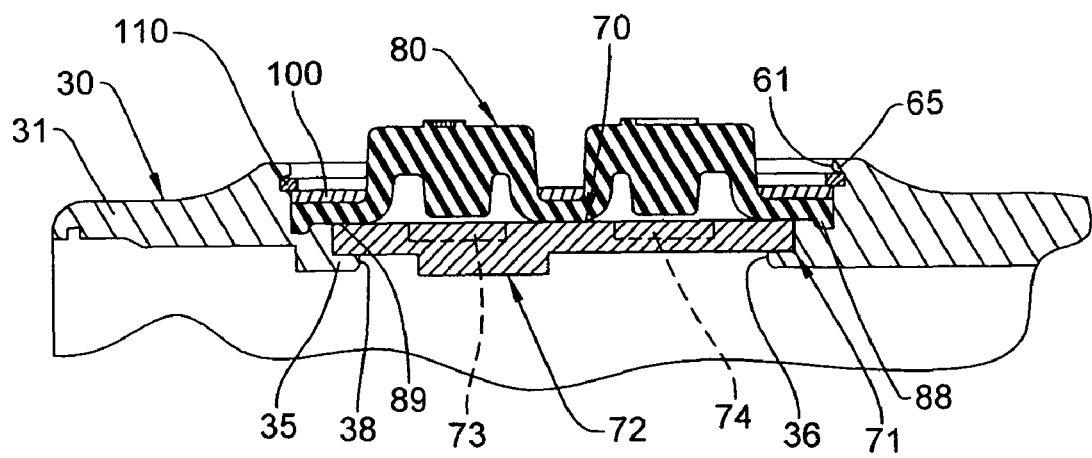
FIG. 11 is an enlarged, fragmentary cross-sectional view of the control arrangement as seen generally along line 11-11 in FIG. 4.

Turning now to control arrangement 20, and with reference to FIGS. 3 and 11, same includes a membrane switch 70 having outer and inner members 71 and 72. Outer member 71 mounts thereon a pair of switch contact pads 73 and 74 which are normally in the open position. Outer member 71 is generally planar and has an outer periphery sized so as to relatively snugly seat within bore portion 42 of housing bore 34 so that outer member 71 rests atop housing flange 35, while inner member 72 projects into innermost bore portion 38. Membrane switch 70 contains suitable circuitry electrically connected to the appropriate components within camera head 13 such that the appropriate control commands are carried out when contact pads 73 and 74 are actuated, as discussed further below.

Figure 7:
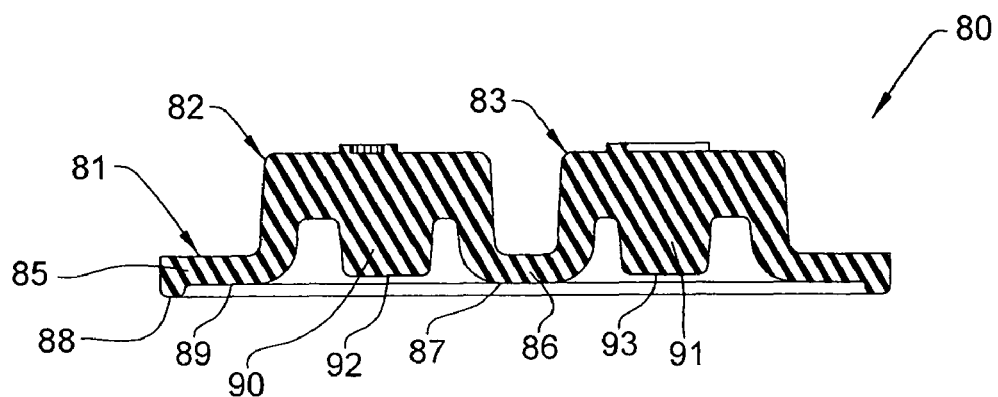
FIG. 7 is an enlarged cross-sectional view of the keypad of the control arrangement as seen generally along line 7-7 in FIG. 3.

Control arrangement 20 additionally includes an actuator or keypad 80, as shown in FIGS. 3, 7 and 11. Keypad 80 has a base member 81 which surrounds and is joined to a pair of raised buttons 82 and 83 which project outwardly from base member 81. Buttons 82 and 83 have respective upper or outer surfaces which include indicia thereon corresponding to various control functions of camera head 13. In the illustrated embodiment, the buttons 82 and 83 respectively include the letters "P" and "W" thereon, which are representative of "picture" and "white balance" functions of camera head 13.

Base member 81 of keypad 80 has an outer annular edge portion 85 which surrounds buttons 82 and 83, and an inner web portion 86 disposed between buttons 82 and 83. Edge portion 85 and web portion 86 are generally coplanar with one another, and in the illustrated embodiment are integrally formed as one-piece with buttons 82 and 83. Web portion 86 includes a lower or inner generally flat surface 87, and outer edge portion 85 includes a lower or inner surface 89 coplanar with surface 87. Outer edge portion 85 defines an annular lip 88 which projects downwardly or inwardly from surface 89.

Buttons 82 and 83 each have respective projections 90 and 91 which are cantilevered downwardly or inwardly and define respective lower or inner surfaces 92 and 93 which are generally planar and coplanar with one another. In the illustrated embodiment, keypad 80 is formed as a one-piece component constructed of an elastomeric and resilient material.

With reference to FIG. 11, keypad 80 is located within bore portion 50 so that lip 88 of base 81 engages within notch 49 and against sealing projection 44 and so that lower surface 89 of base edge portion 85 and lower surface 87 of web 86 seat on the upper surface of membrane switch 70. Further, the lower surfaces 92 and 93 of actuating projections 90 and 91 of keypad 80 are spaced slightly upwardly from the respective contact pads 73 and 74 of membrane switch 70. As shown in FIG. 11, when keypad 80 is assembled to housing 31 atop membrane switch 70, actuating projections 90 and 91 are aligned with contact pads 73 and 74.

Figure 8:
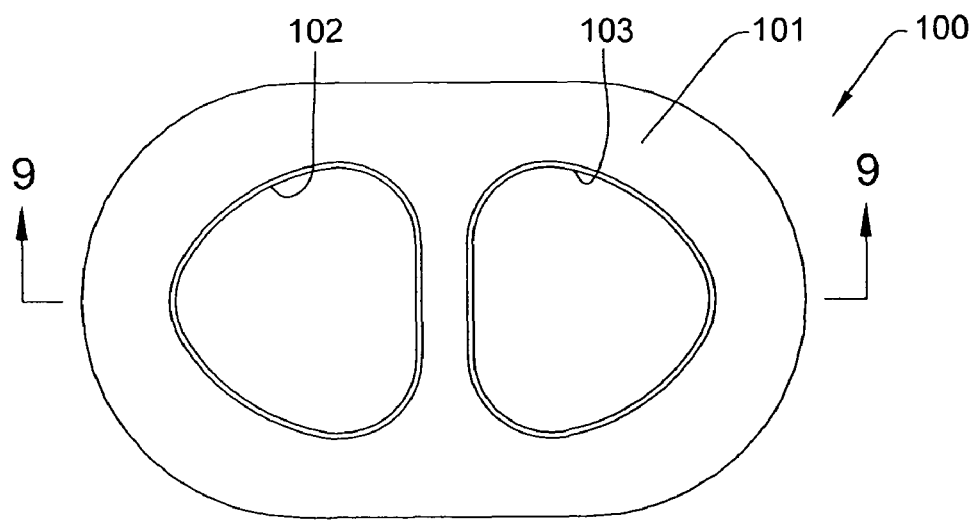
FIG. 8 is an enlarged plan view of the cover plate of the control arrangement.
Figure 9:
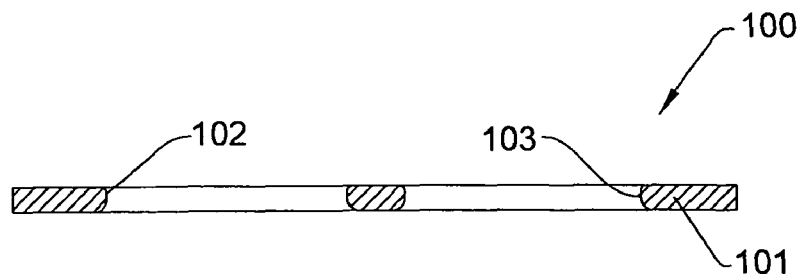
FIG. 9 is an enlarged cross-sectional view of the cover plate as seen generally along line 9-9 in FIG. 8.

Control arrangement 20 additionally includes a cover plate 100 as shown in FIGS. 3 and 8. Cover plate 100 is shaped to cooperate with keypad 80, and includes a planar base wall 101 which defines therein openings 102 and 103 which extend completely through base wall 101 and are shaped to correspond with the outer peripheries of buttons 82 and 83. Buttons 82 and 83 extend upwardly or outwardly through the respective openings 102 and 103 in the assembled condition of control arrangement 20. As shown in FIG. 11, cover plate 100 seats atop base 81 of keypad 80 within bore portion 50, with buttons 82 and 83 of keypad 80 located within the respective openings 102 and 103.

Figure 10:
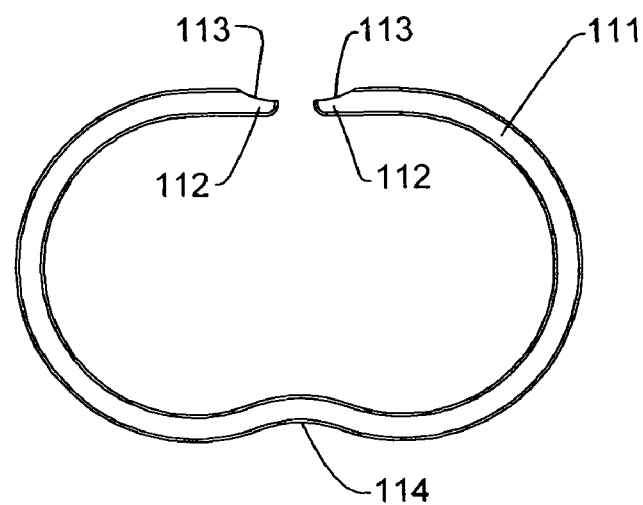
FIG. 10 is an enlarged plan view of the retainer clip of the control arrangement.

With reference to FIGS. 3 and 10, control arrangement 20 additionally includes a retainer clip 110 defined by an elongated body 111 generally having an elliptical shape. Clip body 111 is of a split-ring construction, and thus has a pair of terminal or free ends 112 which are spaced sidewardly from one another to allow compression of clip 110. As shown in FIG. 10, the free ends 112 have chamfers 113 which assist in removing clip 110 from housing 30. Additionally, at the side of clip 110 diametrically opposite from ends 112, body 111 projects inwardly so as to define a recess 114 which aids in installation of clip 110 by allowing easier compression thereof.

Referring to FIG. 11, with membrane switch 70, keypad 80 and cover plate 100 assembled within bore 34 of housing 31, these components of control arrangement 20 are secured within housing 30 via retainer clip 110. Specifically, according to one assembly method, retainer clip 110 is compressed by applying pressure to the opposite sides of body 111 located between ends 112 and recess 114, so that clip 110 can be inserted into and pass through outermost bore portion 61 over flange 65. Once clip 110 has cleared surface 63 of flange 65 which defines bore portion 61, the pressure on clip 110 is removed so that the clip 110 resiliently returns to its normal or at rest configuration (as shown in FIG. 10) and moves into bore portion 60 atop cover plate 100. In this regard, the angled surface 67 of flange 65 serves to guide the clip 110 downwardly during insertion or installation so that same seats within bore portion 60 and is brought into engagement with the cover plate 100. With clip 110 in place within bore 34 of housing 31, clip 110 prevents dislodgement of the underlying components of the control arrangement 20, and also compresses keypad 80 and maintains lip 88 of keypad 80 in notch 39 and in contact with surfaces 48, 45 and 44 of housing 31 so as to effectively create a fluid-tight seal between the external environment and the components internal to housing 31, including membrane switch 70 and the electronic circuitry and other components located within housing 30 of camera head 13. In the illustrated embodiment, the dimensions of flange 88 of keypad 80 are somewhat larger than the dimensions of housing notch 39, such that when keypad 80 is compressed against housing 30 by clip 110 a fluid-tight seal is achieved. Further, the upward tilt of flange 65 of housing wall 31 at surface 67 allows easier insertion of clip 110 into bore 34 of housing 30, and also serves to adjust the depth of the clip 110 downwardly within bore portion 60 and accommodate for varying tolerances of the components of control arrangement 20.

According to another assembly method, the clip 110 can be angled downwardly and one edge of clip 110 can be inserted directly into bore portion 60. The opposite edge of clip 110 is then pushed downwardly past flange 65 and into bore portion 60.

Figure 4:
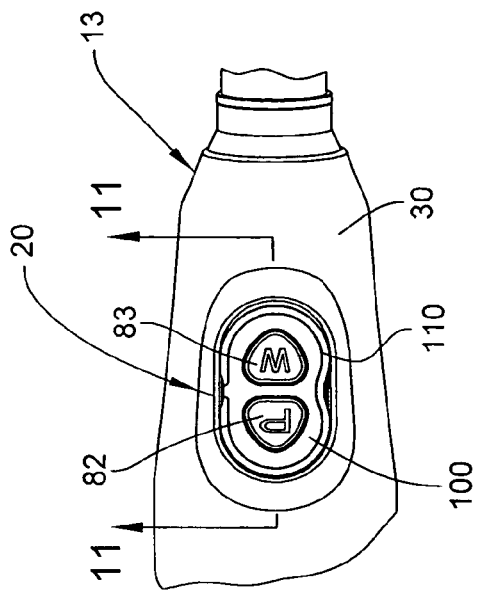
FIG. 4 is an enlarged and fragmentary view of the camera head of the scope assembly.

If desirable or necessary, the control arrangement 20 can be removed from the housing wall 31. Specifically, as shown in FIG. 4, the clip 110 is removed from the housing 30 by inserting a tool behind one or both chamfers 113 of clip 110 and pushing the free ends 112 of clip 110 towards clip recess 114. This action on clip 110 will cause same to disengage from bore portion 60, and allow removal of cover plate 100, keypad 80 and membrane switch 70.

The control or switch arrangement 20 according to the invention as described above self-seals upon assembly of the retainer clip 110 into housing 31, and thus avoids the need for application of a sealing agent, such as silicone, around or within bore 34, which is time-consuming and costly from an assembly perspective. Additionally, the arrangement according to the invention allows disassembly of the control arrangement for purposes of repair or inspection.

It will be appreciated that the scope assembly 11 is shown herein for illustrative purposes only, and various types of surgical tools or instruments other than such scope assembly may incorporate the tool housing structure and control arrangement according to the invention. Some of these types of medical instruments are described above, such as surgical saws, shavers and RF probes. Other types of medical and surgical instruments may utilize the structure of the invention, and thus this invention is not to be construed as limited for use solely in a scope assembly or in the other surgical instruments described herein.

Although a particular preferred embodiment of the invention is disclosed in detail for illustrative purposes, it will be recognized that variations or modifications of the disclosed apparatus, including the rearrangements of parts, lie within the scope of the present invention.

What is claimed is:

1. A surgical instrument comprising:
a housing having a proximal end and a distal end, said distal end being spaced from said proximal end and associated with a surgical tool, said housing including a housing wall defining an opening therein and a sealing surface adjacent said opening; and
a control arrangement for permitting a user to control said instrument and being disposed in said opening, said control arrangement including an actuating member defining a button thereon accessible from an exterior of said housing and associated with a control function of said instrument, a sealing member disposed adjacent said actuating member in said opening, and a retaining clip disposed in said opening to secure said control arrangement to said housing, said retaining clip being compressible to permit installation of said retaining clip into said opening from said exterior of said housing and causing sealing engagement of said sealing member with said sealing surface of said housing wall upon installation of said retaining clip in said opening.

2. The instrument of claim 1, wherein said opening defines a central axis and said retaining clip is disposed in a portion of said opening, said housing defining an annular flange which surrounds said opening at said exterior of said housing, an innermost extent of said flange being disposed closer to the axis than an outermost extent of said portion of said opening in which said retaining clip is disposed to maintain said retaining clip in said opening.

3. The instrument of claim 2, wherein said retaining clip is annular in configuration and is resiliently disposed in said opening.

4. The instrument of claim 1, wherein said opening has a first portion of a first diameter and a second portion of a second diameter greater than said first diameter, said second portion being disposed closer to said exterior of said housing than said first portion, said retaining clip being disposed in said second portion.

5. The instrument of claim 1, wherein said retaining clip causes sealing engagement of said sealing member with said sealing surface of said housing wall without the need for application of a sealing agent at a junction between said housing and said control arrangement.

6. The instrument of claim 1, wherein said sealing member is mounted on said actuating member.

7. The instrument of claim 6, wherein said sealing member and said actuating member are a homogenous, one-piece monolithic component constructed of an elastomeric material.

8. The instrument of claim 1, wherein said opening defines a central axis and said retaining clip is disposed in a portion of said opening, said housing defining a flange at said exterior of said housing adjacent said opening, an innermost terminal edge of said flange being disposed closer to the axis than an outermost surface of said housing wall defining said portion of said opening in which said retaining clip is disposed to maintain said retaining clip in said opening.

9. The instrument of claim 8, wherein said retaining clip is of a split-ring construction so as to be resilient and is compressed during installation thereof into said portion of said opening.

10. The instrument of claim 9, wherein said actuating member mounts thereon said sealing member and said retaining clip compresses said sealing member against said sealing surface.

11. The instrument of claim 1, wherein said opening defines a central axis and said housing wall defines therein a notch, said notch defining a portion of said opening and projecting in a direction generally parallel to the axis and away from said exterior of said housing, said sealing member engaging within said notch and said notch defining at least part of said sealing surface of said housing wall.

12. The instrument of claim 11, wherein said housing wall defines a lip disposed immediately adjacent and radially inwardly of said notch, said lip defining a portion of said opening and projecting in a direction generally parallel to the axis and towards said exterior of said housing, said sealing member including a flange which projects in a direction generally parallel to the axis and into said notch, said lip and said notch together defining said sealing surface of said housing wall.

13. The instrument of claim 12, wherein said sealing member is mounted on said actuating member on a side thereof which faces away from said exterior of said housing.

14. A self-sealing control arrangement for a medical instrument comprising:
a housing for a medical instrument having a housing wall defining a bore therein;
an actuating member disposed in said housing bore for allowing a user to actuate a control function associated with said medical instrument;
a retaining clip disposed in said housing bore closer to an exterior of said housing than said actuating member; and
a sealing member disposed in said housing bore adjacent said actuating member, said retaining clip being compressible to permit installation of said retaining clip into said housing bore from said exterior of said housing and causing sealing engagement of said sealing member with part of said housing wall upon installation of said retaining clip in said housing bore.

15. The control arrangement of claim 14, wherein said bore defines a central axis and said housing wall includes a flange which projects radially inwardly so as to be disposed in overlapping relation with said retaining clip to prevent dislodgement of said retaining clip from said housing bore.

16. The control arrangement of claim 14, wherein said housing bore has a first portion of a first diameter and a second portion of a second diameter greater than said first diameter, said second portion being disposed closer to said exterior of said housing than said first portion, said retaining clip being disposed in said second portion.

17. The control arrangement of claim 14, wherein said retaining clip is of a split-ring construction so as to be resilient and compressible, and causes sealing engagement of said sealing member with said housing wall without the need for application of a sealing agent to a junction between said housing and said control arrangement.

18. The control arrangement of claim 14, wherein said sealing member is mounted on said actuating member.

19. The control arrangement of claim 14, wherein said housing bore defines a central axis and said part of said housing wall defines therein a notch, said notch defining a portion of said housing bore and projecting in a direction generally parallel to the axis and away from said exterior of said housing, said sealing member sealingly engaging within said notch.

20. The control arrangement of claim 19, wherein said housing wall defines a lip disposed immediately adjacent and radially inwardly of said notch, said lip defining a portion of said housing bore and projecting in a direction generally parallel to the axis and towards said exterior of said housing, said sealing member including a flange which projects in a direction generally parallel to the axis and into said notch, said lip and said notch together defining said part of said housing wall.

* * * * *